United States Patent [19]

Mixan

[11] 4,174,394
[45] Nov. 13, 1979

[54] ((5-NITRO-2-THIAZOLYL)THIO) AND ((5-NITRO-2-THIAZOLYL)SULFINYL)PYRAZINES

[75] Inventor: Craig E. Mixan, Midland, Mich.

[73] Assignee: The Dow Chemical Company, Midland, Mich.

[21] Appl. No.: 889,809

[22] Filed: Mar. 24, 1978

[51] Int. Cl.² .................. A61K 31/495; C07D 241/18
[52] U.S. Cl. ..................................... 424/250; 544/405
[58] Field of Search ........................ 544/405; 424/250

[56] References Cited

U.S. PATENT DOCUMENTS 3,850,939 11/1974 Elslager et al. ............. 260/294.8 D
3,870,725 3/1975 Hughes et al. ............... 260/294.8 D Primary Examiner—José Tovar

[57] ABSTRACT

Novel compounds corresponding to the formula

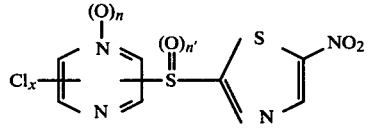

wherein n, n' and x are, individually, 0 or 1. These compounds exhibit utility in the control and kill of bacteria and fungi.

11 Claims, No Drawings

((5-NITRO-2-THIAZOLYL)THIO) AND ((5-NITRO-2-THIAZOLYL)SULFINYL)PYRAZINES

SUMMARY OF THE INVENTION

The novel compounds of the present invention, hereinafter alternatively referred to as "active compounds", correspond to the formula

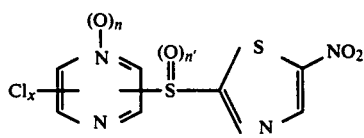

wherein n, n' and x are, individually, 0 or 1.

The active compounds, directly or as active ingredients in formulations and compositions, exhibit, when used in antimicrobially effective amounts, antimicrobial activity against fungi and bacteria. Hereinafter the terms "antimicrobial" and "antimicrobially effective" when used in conjunction with the active compounds will be employed to identify their activity against fungi and/or bacteria.

The invention's novel ((5-nitro-2-thiazolyl)thio)pyrazine compounds are prepared by the reaction of a corresponding chloropyrazine, sodium sulfide nonahydrate and 2-bromo-5-nitrothiazole in dimethylformamide (DMF) as exemplified by the following equation:

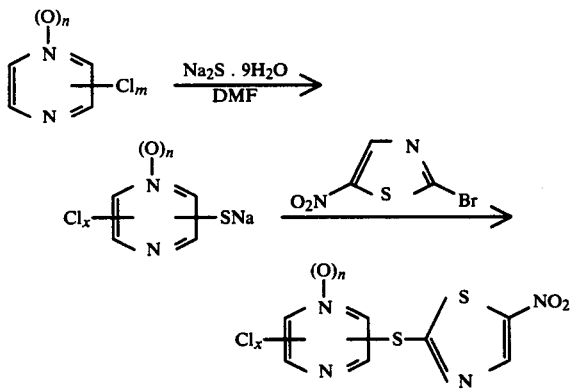

wherein m is 1 or 2 and x and n are as defined hereinbefore, with the proviso that x is always 1 less than m.

The chloropyrazine and the sodium sulfide are stirred from about 20° C. to about 50° C. until the intermediate pyrazine is substantially formed, generally from about 1 to about 16 hours, whereupon the 2-bromo-5-nitrothiazole is added to the reaction mixture. The reaction mixture is maintained at from about 20° C. to about 40° C. with agitation until substantial completion of the reaction, usually from about 1 to about 4 hours. Upon completion of the reaction, the resulting product mass is poured into water and allowed to stand for at least about ½ hour, during which time the desired solid substituted pyrazine product precipitates. The product compound is recovered by filtration, washed and dried and, if desired, can be further purified by conventional techniques known to those skilled in the art. Ordinarily substantial equimolar proportions of the starting materials are employed in the above-described process.

The invention's novel ((5-nitro-2-thiazolyl)sulfinyl)-pyrazine compounds can be prepared by reacting the corresponding ((5-nitro-2-thiazolyl)thio)pyrazine and m-chloroperbenzoic acid in a suitable solvent, such as chloroform. The reaction mixture is maintained at from about 20° C. to about 50° C. with agitation until substantial completion of the reaction, usually from about 1 to about 16 hours. The crude product is recovered by filtering the reaction mixture and washing the filtrate with dilute bicarbonate and water. Evaporation of the solvent provides a solid which can be further purified by conventional techniques known to those skilled in the art.

It is preferred that, in the above-reaction, the molar proportions of m-chloroperbenzoic acid to the ((5-nitro-2-thiazolyl)thio)pyrazine should be in the ratio of at least 1.1 to 1.

DESCRIPTION OF THE PREFERRED EMBODIMENTS

The following examples illustrate the present invention and the manner by which it can be practiced but as such should not be construed as limitations upon the overall scope of the same.

EXAMPLE 1

Preparation of ((5-nitro-2-thiazolyl)thio)Pyrazine (Compound 1)

To a solution of 60.0 g (0.25 mol) of sodium sulfide nonahydrate in 500 ml of dimethyl formamide was gradually added 29 g (0.25 mol) of chloropyrazine in 100 ml of dimethyl formamide. The solution was stirred overnight at approximately 40° C. following which 52.5 g (0.25 mol) of 2-bromo-5-nitrothiazole was added as a solid. This reaction mixture was stirred at room temperature for 4 hours. After this period it was poured into water. The resulting precipitate was collected by suction filtration, washed with water and dried. The crude product was crystallized from methanol to yield 38 g (72% yield) of yellowish-gold crystals, m.p. 129°–130° C. A sample was subjected to elemental analysis. The results obtained were as follows:

Analysis. for $C_7H_4N_4O_2S_2$: Calcd.: C, 35.00; H, 1.67; N, 23.33. Found: C, 34.80; H, 1.71; N, 23.27.

Nuclear magnetic resonance spectroscopy (NMR) confirmed the assigned structure.

The following compounds of Examples 2 through 7 were prepared by the procedures of Example 1. The product compounds were identified by elemental analysis. In each of these Examples NMR confirmed the assigned structure.

EXAMPLE 2

((5-Nitro-2-thiazolyl)thio)pyrazine 1-oxide (Compound 2)

The crude product, prepared from 2-chloropyrazine 1-oxide, was recrystallized from methanol for a 57% yield of yellow crystals, m.p. 145°–146° C., (decomposition).

Analysis. for $C_7H_4N_4O_3S_2$: Calcd.: C, 32.81, H, 1.56; N, 21.88. Found: C, 32.65; H, 1.60; N, 22.05.

EXAMPLE 3

((5-Nitro-2-thiazolyl)thio)pyrazine 4-oxide (Compound 3)

The crude product, prepared from 2-chloropyrazine 4-oxide, was recyrstallized from methanol for a 68% yield of a yellow-gold solid, m.p. 194°–195° C. (decomposition).

Analysis. for $C_7H_4N_4O_3S_2$: Calcd.: C, 32.81; H, 1.56; N, 21.88. Found: C, 32.97, H, 1.75; N, 21.61.

EXAMPLE 4

2-Chloro-3-((5-nitro-2-thiazolyl)thio)pyrazine (Compound 4)

The crude product, prepared from 2,3-dichloropyrazine, was recrystallized from methanol-chloroform for a 45% yield of yellowish-gold crystals, m.p. 139°–141° C.

Analysis. for $C_7H_3ClN_4O_2S_2$: Calcd.: C, 30.60; H, 1.09; N, 20.40. Found: C, 30.74; H, 1.24; N, 20.50.

EXAMPLE 5

2-Chloro-6-((5-nitro-2-thiazolyl)thio)pyrazine (Compound 5)

The crude product, prepared from 2,6-dichloropyrazine, was recrystallized from methanol-chloroform for a 55% yield of yellowish-gold crystals, m.p. 108°–110° C.

Analysis. for $C_7H_3ClN_4O_2S_2$: Calcd.: C, 30.60; H, 1.09; N, 20.40. Found: C, 30.51; H, 1.20; N, 20.58.

EXAMPLE 6

3-Chloro-2-((5-nitro-2-thiazolyl)thio)pyrazine 1-oxide (Compound 6)

The crude product, prepared from 2,3-dichloropyrazine 1-oxide, was recrystallized from methanol for a 50% yield of light brown crystals, m.p. 123°–125° C. (decomposition).

Analysis. for $C_7H_3ClN_4O_3S_2$: Calcd.: C, 28.92; H, 1.03; N, 19.28. Found: C, 29.03; H, 1.14; H, 19.43.

EXAMPLE 7

2-Chloro-6-((5-nitro-2-thiazolyl)thio)pyrazine 1-oxide (Compound 7)

The crude product, prepared from 2,6-dichloropyrazine 1-oxide, was recrystallized from methanol for a 91% yield of a beige solid, m.p. 168°–169.5° C. (decomposition).

Analysis. for $C_7H_3ClN_4O_3S_2$: Calcd: C, 28.92; H, 1.03; N, 19.28. Found: C, 28.62; H, 1.08; N, 19.49.

EXAMPLE 8

((5-Nitro-2-thiazolyl)sulfinyl)pyrazine 1-oxide (Compound 8)

To a stirred solution of 1.0 g (0.004 mol) of Compound 2 in 50 ml of chloroform was gradually added 2.0 g (0.010 mol) of 85% m-chloroperbenzoic acid. The reaction mixture was stirred overnight at room temperature and then filtered. The filtrate was washed with water, dilute bicarbonate and brine, and dried over $MgSO_4$. Evaporation of the solvent afforded a yellow oil that solidified on standing. This crude product was recrystallized from $CHCl_3$/hexane and a second crop of crystals was recrystallized from methanol for a total yield of 0.3 g (28% yield) of yellow crystals, m.p. 139°–141° C.

Analysis. for $C_7H_4N_4O_4S_2$: Calcd.: C, 30.90; H, 1.47; H, 20.59. Found: C, 30.70; H, 1.47; N, 20.14.

NMR and infrared spectroscopy confirmed the assigned structure.

The active compounds of the invention are suitable for use as antimicrobials for the control of bacteria and fungi. This is not to suggest that the active compounds and mixtures thereof with usual additives are equally effective against all such organisms at the same concentration. The active compounds can be employed in an unmodified form or dispersed on a finely divided solid and employed as a dust. Such mixtures can also be dispersed in water with the aid of a surface-active agent and the resulting emulsion employed as a spray. In other procedures, the active compounds can be employed as the active constituents in solvent solutions, oil-in-water or water-in-oil emulsions. The augmented compositions are adapted to be formulated as concentrates and subsequently diluted with additional liquid or solid adjuvants to produce the ultimate treating compositions. Good control and kill have been realized against a number of representative organisms with compositions wherein antimicrobially-effective amounts of from about 0.5 to about 500 parts by weight of one or more of the active compounds per million parts of such compositions are employed. As stated hereinbefore the active antimicrobially-effective amount to be employed against a given organism or in a certain composition can readily be determined by one skilled in the art.

Incorporation of the active compounds of this invention into materials which are subject to fungal attack inhibits the growth of the fungi and preserves the original value of the materials. The active compounds are sufficiently nonvolatile and water-insoluble so that they will persist on or in such materials for long periods of time. Examples of materials which are adversely affected by fungal growth are latex and alkyl paint films, wood and wooden products. The active compounds are sufficiently active against fungi such that only small quantities are required to prevent mildew on paint films or wood rot. The active compounds are therefore useful for long-term protection against fungal growth in or on materials having a wood basis or a protective or decorative paint film or other coating or covering subject to fungal attack.

In a standard activity test, samples of each of Compounds 2 thru 8 were individually dispersed in warm melted nutrient agar which was poured into petri dishes and allowed to solidify, the active compounds being employed in an amount sufficient to provide from 0.5 to 500 parts by weight thereof per million parts (ppm) of the ultimate agar composition. The surface of the agar was inoculated with a variety of bacterial and fungal pest organisms, and the inoculated plates incubated under conditions conducive to bacterial and fungal growth. Similar check plates in which the agar did not contain the active compounds or other toxic compounds were similarly inoculated and incubated.

In these studies, Compounds 2 thru 8 gave 100% growth inhibition (kill) and control of the following organisms, as set forth in Table 1, at the indicated concentrations in parts per million (ppm):

TABLE 1

| | ANTIMICROBIAL ACTIVITY | | | | | | |
|---|---|---|---|---|---|---|---|
| | concentration in ppm | | | | | | |
| Organism | Cmpd 2 | Cmpd 3 | Cmpd 4 | Cmpd 5 | Cmpd 6 | Cmpd 7 | Cmpd 8 |
| S. aureus | * | 1 | 5 | 1 | 0.5 | 5 | 50 |

TABLE 1-continued
ANTIMICROBIAL ACTIVITY
concentration in ppm

| Organism | Cmpd 2 | Cmpd 3 | Cmpd 4 | Cmpd 5 | Cmpd 6 | Cmpd 7 | Cmpd 8 |
|---|---|---|---|---|---|---|---|
| S. typhosa | * | 10 | 5 | 5 | 1 | 5 | 50 |
| A. aerogenes | * | 50 | * | * | 50 | 50 | 50 |
| P. aeruginosa | * | * | * | * | 500 | * | 500 |
| Pseudomonas sp. strain 10 | * | * | * | * | 500 | * | 500 |
| B. subtilis | * | 1 | 5 | 50 | 0.5 | 5 | 5 |
| K. Pneumoniae M-1 | * | 50 | * | 500 | 50 | 50 | 50 |
| S. marcesens | * | 50 | * | 500 | 50 | 50 | 50 |
| C. albicans N | 10 | 50 | 5 | 5 | 50 | 5 | 50 |
| C. albicans D | 10 | 50 | 5 | 5 | 50 | 5 | 50 |
| C. pelliculosa | 5 | 5 | 5 | 0.5 | 50 | 5 | 5 |
| Torulopsis specie | 10 | 10 | 5 | 5 | 10 | 5 | 50 |
| P. pullulans | 5 | 1 | 0.5 | 0.5 | 5 | 5 | 50 |
| C. ips | 5 | 5 | 0.5 | 0.5 | 5 | 5 | 50 |
| T. mentagrophytes | 5 | 5 | 0.5 | 0.5 | 5 | 5 | 5 |
| P. chrysogesum | 5 | 5 | 0.5 | 0.5 | 5 | 5 | 50 |
| Tri-sp-mad-P-42 | 5 | 100 | 50 | 5 | * | 50 | 100 |
| A. Fumigatus | 5 | 5 | 0.5 | 0.5 | 5 | 5 | 50 |
| A. niger | 10 | 5 | 1.0 | 0.5 | 10 | 5 | 50 |

*no kill exhibited at 500 ppm

In a similar agar dilution antimicrobial dilution study, Compound 1 was tested for antimicrobial activity as was, in a comparative operation, its position isomer, 2-((5-Nitro-2-thiazolyl)thio)pyrimidine, which was prepared by the method of Hughes, et al., U.S. Pat. No. 3,870,725.

The results of the study of Compound 1 and the comparative operation with 2-((5-Nitro-2-thiazolyl)thio)pyrimidine are set forth in Table 2. In these studies Compound 1 was shown to be from twice to ten times as active as the pyrimidine compound against 10 of the organisms utilized in the test and at least as effective as the pyrimidine compound against the remainder of the organisms.

TABLE 2

| | Concentration in ppm for 100% Kill | |
|---|---|---|
| Organism | Compound 1 | 2-((5-Nitro-2-thiazolyl)-thio)pyrimidine |
| S. aureus | 1 | 5 |
| S. typhosa | 5 | 5 |
| A. aerogenes | 50 | 50 |
| P. aeruginosa | 500 | 500 |
| Pseudomonas sp. strain 10 | 500 | 500 |
| B. subtilis | 1 | 1 |
| K. Pneumoniae M-1 | 50 | 500 |
| S. marcesens | 50 | 500 |
| C. albicans N | 5 | 5 |
| C. albicans D | 5 | 5 |
| C. pelliculosa | 5 | 5 |
| Torulopsis specie | 1 | 5 |
| P. pullulans | 0.5 | 5 |
| C. ips | 0.5 | 5 |
| T. mentagrophytes | 0.5 | 0.5 |
| P. chrysogesum | 0.5 | 5 |
| Tri.sp.mad.P-42 | 5 | 50 |
| A. fumigatus | 0.5 | 1 |
| A. niger | 0.5 | 5 |

What is claimed is:

1. A compound of the formula

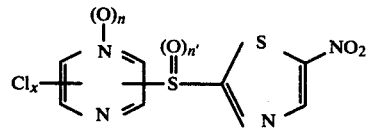

wherein n, n' and x are, individually, 0 or 1.

2. The compound of claim 1 which is ((5-Nitro-2-thiazolyl)thio)pyrazine.

3. The compound of claim 1 which is ((5-Nitro-2-thiazolyl)thio)pyrazine 1-oxide.

4. The compound of claim 1 which is ((5-Nitro-2-thiazolyl)thio)pyrazine 4-oxide.

5. The compound of claim 1 which is 2-Chloro-3-((5-nitro-2-thiazolyl)thio)pyrazine.

6. The compound of claim 1 which is 3-Chloro-2-((5-nitro-2-thiazolyl)thio)pyrazine 1-oxide.

7. The compound of claim 1 which is 2-Chloro-6-((5-nitro-2-thiazolyl)thio)pyrazine.

8. The compound of claim 1 which is 2-Chloro-6-((5-nitro-2-thiazolyl)thio)pyrazine 1-oxide.

9. The compound of claim 1 which is ((5-Nitro-2-thiazolyl)sulfinyl)pyrazine 1-oxide.

10. A method for controlling bacteria or fungi which comprises applying to bacteria and/or fungi or their habitat an antimicrobially-effective amount of a compound of claim 1.

11. A composition for controlling bacteria or fungi comprising an antimicrobially-effective amount of a compound of claim 1.

* * * * *